(12) United States Patent
Oliverius et al.

(10) Patent No.: US 10,016,234 B2
(45) Date of Patent: Jul. 10, 2018

(54) FLEX TIP FLUID LUMEN ASSEMBLY WITH THERMAL SENSOR

(71) Applicant: St. Jude Medical, Cardiology Division, Inc., St. Paul, MN (US)

(72) Inventors: Andrew Oliverius, Eagan, MN (US); Troy T. Tegg, Elk River, MN (US); Zachary Helgeson, Richfield, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 315 days.

(21) Appl. No.: 14/724,169

(22) Filed: May 28, 2015

(65) Prior Publication Data

US 2015/0351832 A1 Dec. 10, 2015

Related U.S. Application Data

(60) Provisional application No. 62/008,196, filed on Jun. 5, 2014.

(51) Int. Cl.
*A61B 18/14* (2006.01)
*A61B 5/00* (2006.01)
*A61B 5/01* (2006.01)
*A61B 18/00* (2006.01)

(52) U.S. Cl.
CPC ........... *A61B 18/1492* (2013.01); *A61B 5/01* (2013.01); *A61B 5/6852* (2013.01); *A61B 2018/00577* (2013.01); *A61B 2018/00821* (2013.01); *A61B 2018/00839* (2013.01)

(58) Field of Classification Search
None
See application file for complete search history.

(56) References Cited

U.S. PATENT DOCUMENTS

| 5,843,076 A * | 12/1998 | Webster, Jr. ....... A61B 18/1492 600/439 |
| 6,078,830 A * | 6/2000 | Levin ................. A61B 18/1492 600/374 |
| 8,187,267 B2 | 5/2012 | Pappone et al. |
| 2005/0090816 A1* | 4/2005 | McClurken ............ A61B 17/32 606/41 |
| 2008/0015570 A1* | 1/2008 | Ormsby ............. A61B 18/1492 606/41 |
| 2010/0152731 A1 | 6/2010 | de la Rama et al. |
| 2012/0157991 A1* | 6/2012 | Christian ........... A61B 18/1492 606/41 |
| 2013/0253504 A1* | 9/2013 | Fang ................. A61B 18/1492 606/41 |
| 2014/0276759 A1* | 9/2014 | Kim .................. A61B 18/1492 606/33 |

* cited by examiner

*Primary Examiner* — Erica Lee
(74) *Attorney, Agent, or Firm* — Dykema Gossett PLLC

(57) ABSTRACT

A catheter tip is disclosed comprising a proximal stem that comprises a lumen. An electrode wall that comprises a center cavity can be coupled to the distal end of the proximal stem. An electrode cap can be coupled to a distal end of the electrode wall. An elongate thermocouple element can extend through the lumen of the proximal stem and the center cavity and can be coupled to the electrode cap. The elongate thermocouple element can be turned around a portion of a longitudinal axis defined by the catheter tip assembly.

19 Claims, 5 Drawing Sheets

FLEX TIP FLUID LUMEN ASSEMBLY WITH THERMAL SENSOR

CROSS-REFERENCE TO RELATED APPLICATIONS

This application claims the benefit of U.S. provisional application No. 62/008,196, filed 5 Jun. 2014, which is hereby incorporated by reference as though fully set forth herein.

BACKGROUND a. Field

The instant disclosure relates generally a flex tip fluid lumen assembly with thermal sensor.

b. Background Art

Medical devices, catheters, and/or cardiovascular catheters, such as electrophysiology catheters, are used in a variety of diagnostic, therapeutic, and/or mapping and ablative procedures to diagnose and/or correct conditions such as atrial arrhythmias, including for example, ectopic atrial tachycardia, atrial fibrillation, and atrial flutter. Arrhythmias can create variety of conditions including irregular heart rates, loss of synchronous atrioventricular contractions and stasis of blood flow in a chamber of a heart, which can lead to a variety of symptomatic and asymptomatic ailments and even death.

Typically, a catheter is deployed and manipulated through a patient's vasculature to the intended site, for example, a site within a patient's heart or a chamber or vein thereof. To position a catheter within the body at a desired site, some type of navigation must be used, such as using mechanical steering features incorporated into the catheter (or an introducer sheath). In some examples, medical personnel may manually manipulate and/or operate the catheter using the mechanical steering features.

In order to facilitate the advancement of catheters through a patient's vasculature, the simultaneous application of torque at the proximal end of the catheter and the ability to selectively deflect the distal tip of the catheter in a desired direction can permit medical personnel to adjust the direction of advancement of the distal end of the catheter and to position the distal portion of the catheter during an electrophysiological procedure. The proximal end of the catheter can be manipulated to guide the catheter through a patient's vasculature. The distal tip can be deflected by a pull wire attached at the distal end of the catheter that extends to a control handle that controls the application of tension on the pull wire.

A medical procedure in which an electrophysiology catheter is used includes a first diagnostic catheter deployed through a patient's vasculature to a patient's heart or a chamber or vein thereof. An electrophysiology catheter that carries one or more electrodes can be used for cardiac mapping or diagnosis, ablation and/or other therapy delivery modes, or both. Once at the intended site, treatment can include radio frequency (RF) ablation, cryoablation, laser ablation, chemical ablation, high-intensity focused ultrasound-based ablation, microwave ablation, etc. An electrophysiology catheter imparts ablative energy to cardiac tissue to create one or more lesions in the cardiac tissue and oftentimes a contiguous or linear and transmural lesion. This lesion disrupts undesirable cardiac activation pathways and thereby limits, corrals, or prevents stray conduction signals that can form the basis for arrhythmias.

Because RF ablation can generate significant heat, which if not controlled can result in excessive tissue damages, such as steam pop, tissue charring, and the like, it can be desirable to monitor the temperature of ablation electrode assemblies. It can also be desirable to include a mechanism to irrigate the ablation electrode assemblies and/or targeted areas in a patient's body with biocompatible fluids, such as saline solution. The use of irrigated ablation electrode assemblies can also prevent the formation of soft thrombus and/or blood coagulation, as well as enable deeper and/or greater volume lesions as compared to conventional, non-irrigated catheters at identical power settings.

The foregoing discussion is intended only to illustrate the present field and should not be taken as a disavowal of claim scope.

BRIEF SUMMARY

In various embodiments, a catheter tip assembly can comprise a proximal stem that includes a lumen. An electrode wall that comprises a center cavity can be coupled to the distal end of the proximal stem and an electrode cap can be coupled to a distal end of the electrode wall. An elongate thermocouple can extend through the lumen of the proximal stem and the center cavity and can be coupled to the electrode cap. The elongate thermocouple can be turned around a portion of a longitudinal axis defined by the catheter tip assembly. In some embodiments, the elongate thermocouple can be turned around the portion of the longitudinal axis in a range of 0.2 and 1 turn. The elongate thermocouple can be turned around the portion of the longitudinal axis between a distal end of the proximal stem and a proximal end of the electrode cap. In some embodiments, a catheter shaft can be coupled to a proximal end of the proximal stem and the elongate thermocouple can extend from the electrode cap through a lumen of the catheter. In some embodiments, a coil can extend between the distal end of the proximal stem and the proximal end of the electrode cap and can have a spring three in a range of 15 to 100 grams. In some embodiments, a fluid lumen manifold can extend through the lumen of the proximal stem and the elongate thermocouple can be turned around a portion of the fluid lumen manifold. The elongate thermocouple can be adhered to the electrode cap and the proximal stem. In some embodiments, the elongate thermocouple can be inserted within a lumen of a formed polymer tube and a distal end of the formed polymer tube can be located within an electrode pocket in the electrode cap.

In various embodiments, a catheter can comprise a proximal stem that comprises a manifold lumen and a thermocouple lumen. An electrode wall that comprises a center cavity can be in communication with the manifold lumen and the thermocouple lumen. In some embodiments, the electrode wall can be coupled to a distal end of the proximal stem. An electrode cap can be coupled to a distal end of the electrode wall. In some embodiments, a fluid lumen manifold that can extend through the manifold lumen a defined distance into the center cavity. An elongate thermocouple can extend through the thermocouple lumen and can be coupled to the electrode cap and the elongate thermocouple can be turned around a portion of the fluid lumen manifold. In some embodiments, the elongate thermocouple can be turned around the portion of the fluid lumen manifold between a distal end of the proximal stem and a proximal end of the electrode cap. A catheter shaft can be coupled to a proximal end of the proximal stem and the elongate thermocouple can extend through the catheter shaft to a proximal end of the catheter shaft. In some embodiments, a coil can be located in the center cavity and can extend between the distal end of the proximal stem and the proximal end of the electrode cap. The coil can encircle the elongate thermocouple and the fluid lumen manifold. In some embodiments, the manifold lumen and the thermocouple lumen can be connected and in some embodiments, the manifold lumen and the thermocouple lumen can be separate.

In various embodiments, a flexible tip electrode can comprise a proximal stem that comprises a manifold lumen and a thermocouple lumen. A flexible electrode wall that comprises a center cavity and a linear gap can be coupled to the distal end of the proximal stem. An electrode cap can be coupled to a distal end of the flexible electrode wall and a fluid lumen manifold can extend through the manifold lumen a defined distance into the center cavity. In some embodiments, an elongate thermocouple element can extend through the thermocouple lumen and can be coupled to the electrode cap. The elongate thermocouple can be turned around a portion of the fluid lumen manifold in a range of 0.2 to 1 turn. A coil can be located in the center cavity that extends between the distal end of the proximal stem and a proximal end of the electrode cap and can encircle the fluid lumen manifold and the elongate thermocouple element. In some embodiments, the electrode cap can comprise an electrode pocket formed in a distal face of the electrode cap that is in communication with the center cavity and a temperature sensing component of the thermocouple element can be adhered in the electrode pocket formed in the distal face of the electrode cap. In some embodiments, the elongate thermocouple can be inserted into a polymer tube.

The foregoing and other aspects, features, details, utilities, and advantages of the present disclosure will be apparent from reading the following description and claims, and from reviewing the accompanying drawings.

DETAILED DESCRIPTION

Figure 1:
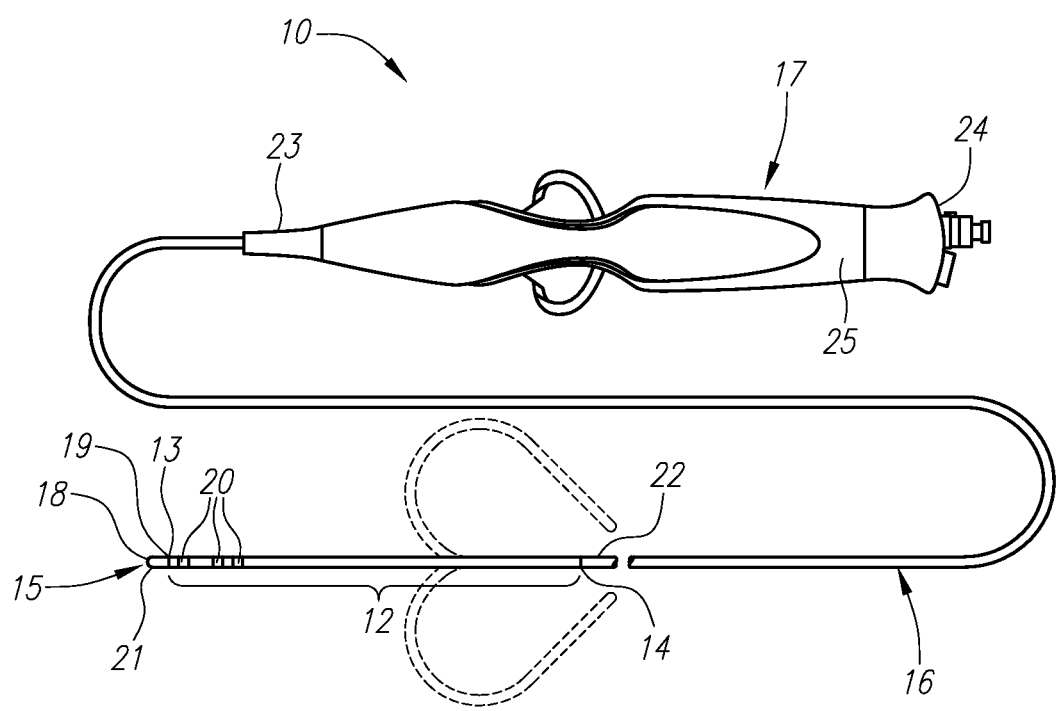
FIG. 1 illustrates a deflectable electrophysiology catheter that comprises a deflectable catheter shaft section, in accordance with embodiments of the present disclosure.

FIG. 1 illustrates a deflectable electrophysiology catheter that comprises a deflectable catheter shaft section in accordance with embodiments of the present disclosure. Deflectable catheter shaft section 12 includes an elongated body having a distal end 13 and a proximal end 14. In its most general form, catheter 10 further includes a tip assembly 15 located at the distal end 13 of the deflectable catheter shaft section 12, a proximal catheter shaft section 16 located at the proximal end 14 of the deflectable catheter shaft section 12, and a handle assembly 17. Catheter 10 may be used in any number of diagnostic and/or therapeutic applications, such as the recording of electrograms in the heart, the performance of a cardiac ablation procedure, and other similar applications/procedures. Accordingly, one of ordinary skill in the art will recognize and appreciate that the inventive deflectable catheter shaft section and method of manufacturing the same can be used in any number of diagnostic and therapeutic applications.

The deflectable catheter shaft section 12 is disposed between the tip assembly 15 and the proximal catheter shaft section 16 and can include a plurality of ring electrodes 20. The length and diameter of the deflectable catheter shaft section 12 can vary according to the application. Generally, the length of the deflectable catheter shaft section 12 can range from about 2 inches (18.8 mm) to about 6 inches (119.4 mm) and the diameter of the deflectable catheter shaft section 12 can range from about 5 French to about 12 French. The diameter of the deflectable catheter shaft section 12 can be about 7 French in accordance with some embodiments. Although these particular dimensions are mentioned in particular, the dimensions of the deflectable catheter shaft section 12 can vary in accordance with various applications of the deflectable catheter shaft section 12. The deflectable catheter shaft section 12 can be configured for deflection independent of the proximal catheter shaft section 16.

The tip assembly 15 comprises a tip electrode 21 having a distal end 18 and a proximal end 19. Tip electrode 21 may be configured for various functions and may include, without limitation, an active outer surface that is configured for exposure to blood and/or tissue. The tip electrode 21 may be affixed to distal end 13 of the deflectable catheter shaft section 12 in a number of ways. For instance, the tip electrode 21 may be bonded to an inner radial surface of the deflectable catheter shaft section 12 using an epoxy material. As used herein, the term "radial surface" means a surface at a radial distance from a central axis or a surface developing uniformly around a central axis (for example, but without limitation, an arcuate surface, an annular surface, or a cylindrical surface). The tip electrode 21 of the tip assembly 15 may have a recess formed therein that is sufficiently sized and configured to receive a wire that is connected to the tip electrode 21, as discussed herein. One end of the wire can be connected to the tip electrode 21 and the other end can be connected to, for example, monitoring or recording or ablation devices, such as a radiofrequency (RI) generator. The wire can be a pre-coated wire that is insulated from other components in the tip assembly 15. The tip electrode 21 of the tip assembly 15 may further include a lumen formed therein that is configured to receive a thermal sensor, as discussed herein. The thermal sensor may be configured to measure the temperature of the tip electrode 21, targeted tissue, and/or the interface therebetween and provide feedback to the monitoring or recording or ablation devices described hereinabove. The tip electrode 21 may further include a fluid lumen manifold configured as a passageway for irrigation fluid.

The proximal catheter shaft section 16 can also include one or more lumens. The proximal catheter shaft section 16 can be constructed of a series of polymer layer(s) and braid structure(s). In particular, one or more wires wound to form a cylindrical braid structure can substantially surround the one or more lumens of proximal catheter shaft section 16. In addition, a polymeric material, such as polyurethane, nylon, or various types of plastic materials such as polyether block amides offered under the trademark PEBAX®, or any other suitable material, can also substantially surround the one or more lumens of proximal catheter shaft section 16. The material can have the capability to be displaced and/or to shrink when subjected to a process, such as for example, a heating process that is performed. The mechanical properties of the proximal catheter shaft section 16 can also be varied by varying the properties of the cylindrical braid structure(s) and the polymeric material (e.g., dimension of the cylindrical braid structure and/or durometers of the polymers). Additionally, the mechanical properties of the proximal catheter shaft section 16, can be varied along the length of the proximal catheter shaft section 16 in accordance with some embodiments of the disclosure. Alternatively, the mechanical properties of the proximal catheter shaft section 16 can be substantially constant along the entire length of the proximal catheter shaft section 16, in accordance with some embodiments of the disclosure.

The handle assembly 17 can be coupled to the proximal catheter shaft section 16 at its proximal end (disposed within handle assembly 17 and not shown). The handle assembly 17 can be operative to, among other things, effect movement (i.e., deflection) of the deflectable catheter shaft section 12. The handle assembly 17 includes a distal end 23 and a proximal end 24. The handle assembly 17 includes an actuator that can be selectively manipulated to cause deflectable catheter shaft section 12 to deflect in one or more directions (e.g., up, down, left, and right). Deflectable catheter shaft section 12 may be configured for unidirectional deflection in accordance with some embodiments and may be configured for bi-directional deflection in accordance with other embodiments.

The catheter 10 may include any number of other elements such as, for example and without limitation, thermocouples, thermistor temperature sensors, etc. for monitoring the temperature of targeted tissue and controlling the temperature. In some embodiments, the catheter 10 can include a sensor for producing signals indicative of catheter location information, and may include one or more electrodes. In an example, the catheter 10 may include ring electrodes 20 that collectively define the sensor. The one or more electrodes may be provided on a distal end 13 of the catheter 10 and a localization system (e.g., EnSite™ Velocity™ system) may compute a distal location of the catheter 10 using received location information from the one or more electrodes and/or a geometrical relationship between the one or more electrodes.

Figure 2A:
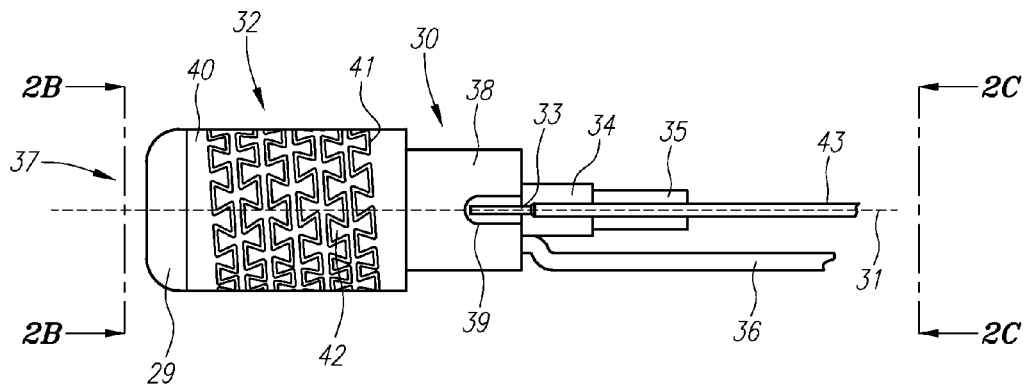
FIG. 2A illustrates a flexible tip assembly, in accordance with embodiments of the present disclosure.

In various embodiments, the catheter 10 can include a flexible tip assembly, which can include, for example, a flexible tip electrode from a Therapy™ Cool Flex™ ablation catheter manufactured by St. Jude Medical, Inc. of St. Paul, Minn. Additional details regarding a flexible electrode tip may be found in, for example, U.S. Pat. No. 8,187,267 B2 and United States patent application publication no. US 2010/0152731 A1, each of which is hereby incorporated by reference as though fully set forth herein. One embodiment of a flexible tip assembly 30 is illustrated in FIG. 2A. The flexible tip assembly 30 has a longitudinal axis 31 and can comprise a flexible tip electrode 32, an electrode wire 33, a stop tube 34, a fluid lumen manifold 35, and a thermal sensor 36. The flexible tip electrode 32 can comprise a tip electrode distal end 37, a proximal stem 38, a recess 39, and an electrode wall 40. The electrode wall 40 can be formed of a radial surface and can include at least one linear gap 41. The at least one linear gap 41 can extend along an outer radial surface of the flexible tip electrode 32 and can form a variety of patterns on the outer radial surface of the flexible tip electrode 32, allowing for the flexible tip electrode 32 to flex and/or deform to some degree when a force is exerted on a tip of the flexible tip electrode 32, for example. In one embodiment, the pattern is an interlocking dovetail pattern. The interlocking dovetail pattern can comprise a plurality of blocks 42 wherein each of the blocks comprises a head 50 and a neck 51 (see FIG. 3). Alternatively, in some embodiments, the pattern can be any type of interlocking arrangement that provides for relative movement in the proximal and distal direction with regard to either all or part of flexible tip assembly 30. For example, alternative patterns of the interlocking arrangement can be bulbous, trapezoidal, triangular, rectangular, and any other shape that creates an interlocking fit.

The electrode wire 33 can be coupled to the recess 39 of the flexible tip electrode 32. The electrode wire 33 can be coupled to the flexible tip electrode 32 by soldering, adhesive, or other methods known in the art. The electrode wire 33 can be surrounded along part of its length by a wire coating 43. The wire coating 43 can electrically insulate the electrode wire 33 from other components of the catheter. The electrode wire 33 can be connected to, for example, monitoring or recording or ablation devices, such as a radiofrequency (RF) generator.

The electrode distal end 37 can include an electrode cap 29, which can be coupled to a distal end of the electrode wall 40. The thermal sensor 36 can be positioned within an opening that passes from the distal end of the electrode cap 29 to the proximal end of the electrode cap 29 and can be used to monitor the operating temperature of the flexible tip electrode 32 or the temperature of tissue adjacent the flexible tip electrode 32. The fluid lumen manifold 35 can extend through the manifold lumen a defined distance into the center cavity. The stop tube 34 may be coupled to the fluid lumen manifold 35 and configured to interact with a portion of the flexible tip electrode 32 to control the distance that a distal end of the fluid lumen manifold 35 can extend into the flexible tip electrode 32.

Figure 2B:
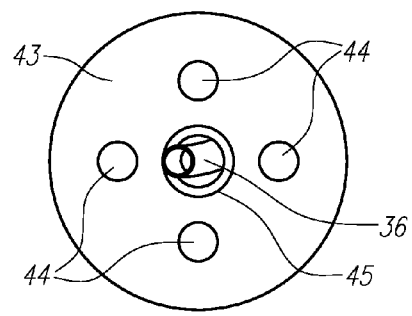
FIG. 2B illustrates an end view taken in the direction of line 2B-2B of FIG. 2A, in accordance with embodiments of the present disclosure.

FIG. 2B illustrates an end view taken in the direction of line 2B-2B of FIG. 2A, in accordance with embodiments of the present disclosure. In some embodiments, the electrode cap includes a plurality of irrigation ports 44 that pass through the electrode cap 29. The electrode cap 29 includes an electrode pocket 45, that can be configured to receive a distal end of the thermal sensor 36. As illustrated in FIG. 2B, the distal end of the thermal sensor 36 can be seen protruding into the electrode pocket 45. In some embodiments, the thermal sensor 36 can be adhered within the electrode pocket 45 in the electrode cap 29.

Figure 2C:
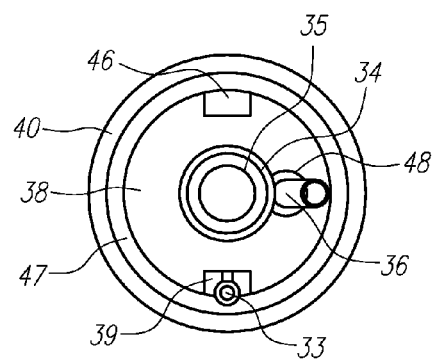
FIG. 2C illustrates an end view taken in the direction of line 2C-2C of FIG. 2A, in accordance with embodiments of the present disclosure.
Figure 4:
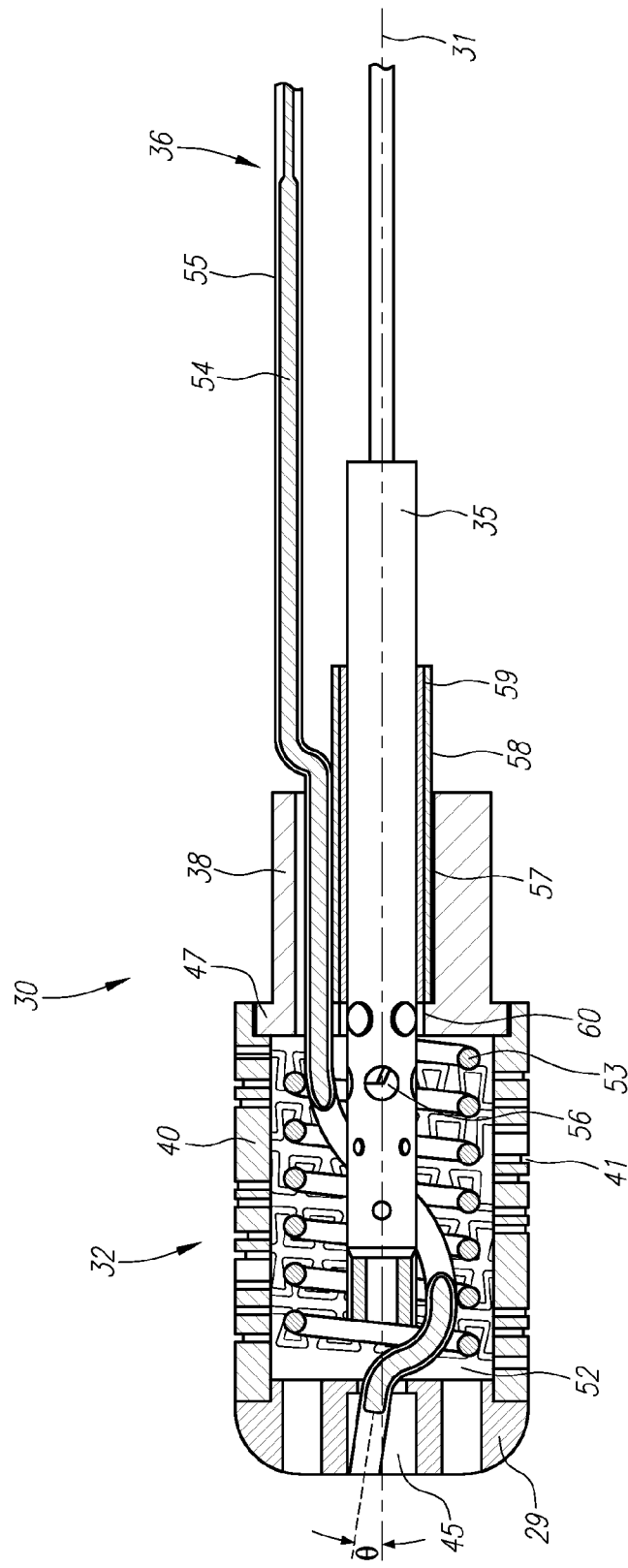
FIG. 4 illustrates a cross-sectional view of the embodiment seen in FIG. 3 taken along line 4-4, in accordance with embodiments of the present disclosure.

FIG. 2C illustrates an end view taken in the direction of line 2C-2C of FIG. 2A, in accordance with embodiments of the present disclosure. In some embodiments, the electrode wall 40 can be coupled to the proximal stem 38 via a mounting lip 47, which can be formed around a perimeter of the proximal stem 38, at the distal end of the proximal stem 38 (as shown in FIG. 4). The proximal end of the proximal stem 38 can be coupled to the proximal catheter shaft section 16. In an example, a portion of the outer surface of the proximal stem 38 can be adhered to an inner surface of the proximal catheter shaft section 16.

The proximal stem 38 can include one or more recesses 39 sized and configured to receive the electrode wire 33, which can be soldered to a distal end of the recess 39, in some embodiments. The proximal stem 38 can include a lumen through which the stop tube 34 passes and the stop tube 34 can include a lumen through which the fluid lumen manifold 35 passes. In addition, the proximal stem 38 can include a thermocouple lumen 48 through which the thermal sensor 36 can pass. In some embodiments, the thermal sensor 36 can be an elongate thermocouple and can pass from a proximal end of the proximal catheter shaft section 16, through a lumen of the proximal catheter shaft section 16, the thermocouple lumen 48 of the proximal stem 38, a center cavity of the electrode wall 40, and can be adhered within the electrode pocket 45 of the electrode cap 29.

Figure 3:
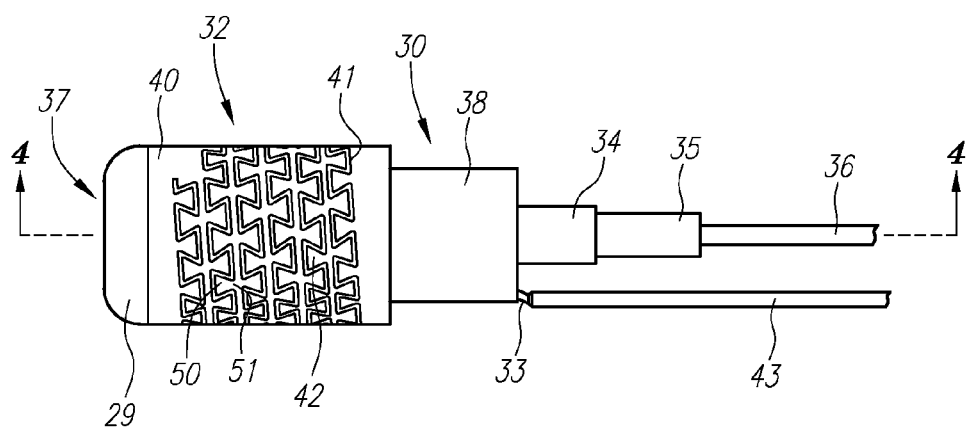
FIG. 3 illustrates the flexible tip assembly seen in FIG. 2A rotated 90 degrees about a longitudinal axis of the flexible tip assembly, in accordance with embodiments of the present disclosure.

FIG. 3 illustrates the flexible tip assembly shown in FIG. 2A rotated 90 degrees about a longitudinal axis of the flexible tip assembly, in accordance with embodiments of the present disclosure. The electrode wire 33 and the wire coating 43 covering a portion of the electrode wire 33 is illustrated traveling parallel to a longitudinal axis of the flexible tip assembly 30. The wiring of thermal sensor 36 is illustrated traveling parallel to the longitudinal axis of the flexible tip assembly 30 through the proximal stem 38 and the electrode wall 40, to the electrode cap 29. In the illustrated configuration, the wiring of the thermal sensor 36 is offset from the electrical wire 43 by 90 degrees around the outer radial surface of the flexible tip electrode 32.

The electrode wall 40 can include at least one linear gap 41. The at least one linear gap 41 can extend along an outer radial surface of the flexible tip electrode 32 and can form a variety of patterns on the outer radial surface of the flexible tip electrode 32. In one embodiment, the pattern can be an interlocking dovetail pattern. The interlocking dovetail pattern can include a plurality of blocks 42 wherein each of the blocks includes a head 50 and a neck 51. Alternatively, as discussed herein, the pattern can be any type of interlocking arrangement that provides for relative movement in the proximal and distal direction with regard to either all or part of tip assembly 15.

The electrode wire 33, surrounded by wire coating 43, is coupled to the recess of the flexible tip electrode 32. As discussed herein, the distal end of thermal sensor 36 can be adhered within the electrode pocket of the electrode cap and can be used to monitor the operating temperature of the flexible tip electrode 32 and/or the temperature of tissue adjacent the flexible tip electrode 32. The stop tube 34 may be coupled to the fluid lumen manifold 35 and configured to interact with a portion of the flexible tip electrode 32 to control the distance that a distal end of the fluid lumen manifold 35 can extend into the flexible tip electrode 32, FIG. 4 illustrates a cross-sectional view of the embodiment illustrated in FIG. 3 taken along line 4-4, in accordance with embodiments of the present disclosure. The flexible tip electrode 32 can include a center cavity 52, a coil 53, an electrode wall 40, at least one linear gap 41, the proximal stein 38 with mounting lip 47, and the thermal sensor 36. The thermal sensor 36 can pass through the thermocouple lumen 48 of the proximal stem 38 and through the center cavity 52 in the electrode wall 40 and the distal end of the thermal sensor 36 can be adhered in the electrode pocket 45. The center cavity 52 can be in communication with the electrode pocket 45 and can also be in communication with the thermocouple lumen 48 and manifold lumen of the proximal stem 38. In some examples, the thermocouple lumen 48 and the manifold lumen can be connected and form a single lumen. Alternatively, the thermocouple lumen 48 and the manifold lumen can be separated (e.g., by a portion of the proximal stem 38) and form separate lumens.

In some embodiments, the thermal sensor 36 can be turned or wrapped around a portion of a longitudinal axis 31, defined by the catheter tip assembly 30. In an example, at least one linear gap 41 can allow the flexible tip electrode 32 to compress longitudinally along the longitudinal axis 31 defined by the catheter tip assembly 30 and/or move laterally and/or angularly with respect to the longitudinal axis 31. The thermal sensor 36 can be adhered within the thermocouple lumen 48 of the proximal stem 38 and within the electrode pocket 45. As such, when the flexible tip electrode 32 flexes, the portion of the thermal sensor 36 passing through the center cavity 52 of the flexible tip electrode 32 can flex.

In some prior approaches, the portion of the thermal sensor 36 passing through the center cavity 52 runs linearly from the proximal stem 38 to the electrode pocket 45 (e.g., parallel to the longitudinal axis 31). In an example, the thermal sensor 36 passes through the center cavity 52 linearly (e.g., without a bend in the thermal sensor 36). a result, a stress point can occur where the thermal sensor 36 exits the thermocouple lumen 48 of the proximal stem 38 and enters the center cavity 52. In addition, a stress point can occur where the thermal sensor 36 enters the electrode pocket 45 from the center cavity 52. In some examples, because the thermal sensor 36 is run linearly from the proximal stem 38 to the electrode pocket 45, minimal slack is present in the thermal sensor 36, which can cause the thermal sensor 36 to bend and create stress points where the thermal sensor 36 exits the thermocouple lumen 48 of the proximal stem 38 and enters the center cavity 52 and where the thermal sensor 36 enters the electrode pocket 45 from the center cavity 52. For example, the thermal sensor 36 can bend as a result of the longitudinal compression and/or lateral and/or angular movement of the flexible tip electrode 32. Other prior approaches have placed a thermal sensor in the proximal stem 38 to reduce stress exerted on the thermal sensor 36. However, placing the thermal sensor 36 in the proximal stem 38 can result in an inaccurate temperature reading of the flexible tip electrode 32 and/or tissue adjacent the flexible tip electrode 32, because of a lack of proximity to those areas.

Accordingly, embodiments of the present disclosure can include routing the thermal sensor 36 through the center cavity 52 in a way that avoids causing stress points, for example, where the thermal sensor 36 exits the thermocouple lumen 48 of the proximal stem 38 and enters the center cavity 52 and where the thermal sensor 36 enters the electrode pocket 45 from the center cavity 52. In some embodiments, the thermal sensor 36 is turned or wrapped at least partially around a portion of the longitudinal axis 31 defined by the catheter tip assembly 30. In an example, the thermal sensor 36 can be turned or wrapped around the portion of the longitudinal axis 31 between the distal end of the proximal stem 38 and the proximal end of the electrode cap 29. The thermal sensor 36 may, for example, be turned or wrapped around the portion of the longitudinal axis 31 in a range of 0.2 to 1 rotation. In some embodiments, the thermal sensor 36 can be turned around the portion of the longitudinal axis 31 in a range of 0.3 to 0.6 rotations. In some embodiments, however, the thermal sensor 36 may, for example, be turned or wrapped around the portion of the longitudinal axis 31 greater than 1 rotation. For example, As a result of the thermal sensor 36 being turned or wrapped around the portion of the longitudinal axis 31, the length of the thermal sensor 36 spanning the center cavity 52 is longer than that of some prior approaches. The increased length of the thermal sensor 36 passing through the center cavity 52 can allow for the thermal sensor 36 to flex over a greater length, thus reducing stress points where, for example, the thermal sensor 36 exits the thermocouple lumen 48 of the proximal stem 38 and enters the center cavity 52 and/or where the thermal sensor 36 enters the electrode pocket 45 from the center cavity 52. In an example, because the thermal sensor 36 is turned or wrapped around the portion of the longitudinal axis 31, the portion of the thermal sensor 36 in the center cavity can be compressed and can flex along the turned portion of the thermal sensor 36, as the flexible tip electrode 32 is compressed.

In addition, as a result of the thermal sensor 36 being turned or wrapped around the portion of the longitudinal axis 31, internal biasing of the flexible tip electrode 32 may be alleviated. For example, in prior approaches where the thermal sensor 36 passes through the center cavity linearly, the thermal sensor 36 may be less flexible. This can result in the flexible tip electrode 32 being deflected in a particular direction upon exertion of force upon the flexible tip electrode 32. For example, the flexible tip electrode 32 may deflect laterally when a longitudinal force is exerted on the flexible tip electrode 32. In addition, where the flexible tip electrode 32 does not have any force exerted on its tip, the linearly run thermal sensor 36 can create a biasing force that deflects the flexible tip electrode 32 in a particular direction away from a neutral position (e.g., where no biasing force is present). Embodiments of the present disclosure can provide a more flexible thermal sensor 36, which can distribute the biasing force over the turned portion of the thermal sensor. As such, when a force is exerted on the tip of the flexible tip electrode, deflection of the flexible tip electrode 32 may not be affected by the thermal sensor 36. In addition, where the flexible tip electrode 32 does not have any force exerted on its tip, the turned thermal sensor 36 can alleviate the biasing force, allowing the flexible tip electrode 32 to remain in a more neutral position.

In some embodiments, the thermal sensor 36 can be pre-formed to maintain the turn in the thermal sensor 36. In an example, the thermal sensor 36 can include an elongate thermocouple 54, such as a T-type or K-type thermocouple, for example, that can be sized and configured to be placed in a polymer (e.g., polyimide) tube 55. The polymer tube 55 can be formed using a spin formed nitinol wire, in some examples. The nitinol wire can be inserted into the polymer tube 55 and heat can be applied to the polymer tube 55 and/or the nitinol wire to introduce the turn into the polymer tube 55, as discussed herein. In some examples, air heated to 600 degrees Fahrenheit (° F.) can be blown across the polymer tube 55 that has the nitinol wire inserted within for a time period in a range of 15 to 30 seconds.

In an example, the elongate thermocouple 54 can be brined of 44 American Wire Gauge (AWG) wire and can be inserted into a proximal end of the polymer tube 55 such that the elongate thermocouple 54 extends approximately 2 inches from a distal end of the polymer tube 55. The exposed end of the elongate thermocouple 54 can be submerged into a pool of adhesive (e.g., M11 adhesive) and the distal end of the elongate thermocouple 54 can be drawn back within the polymer tube 55 until a solder joint at the distal end of the elongate thermocouple 54 is positioned within the polymer tube 55 (e.g., at a distal end of the polymer tube 55). In some embodiments, the elongate thermocouple 54 can be inserted into the polymer tube 55, such that the solder joint is positioned within the polymer tube 55 and a syringe can be used to inject the adhesive into the polymer tube 55. By injecting the adhesive into the polymer tube 55, any air bubbles that remain in the adhesive within the polymer tube can be forced out of the polymer tube 55. In some embodiments, upon introducing the adhesive into the space between the elongate thermocouple 54 and the polymer tube 55, the thermal sensor 36 can be placed in an oven to cure the adhesive at a temperature in a range of 135 to 150° F. for a time in a range of 15 to 20 minutes, in an example.

In some embodiments, the thermal sensor 36 can be positioned in the catheter tip assembly 30, such that the thermal sensor 36 passes through the thermocouple lumen 48, through the center cavity 52, and into the electrode pocket 45. In an example, where the thermal sensor 36 includes an elongate thermocouple 54, the temperature sensing component of the elongate thermocouple 54 can be inserted into the electrode pocket 45 formed in the distal face of the electrode cap 29. For instance, the temperature sensing component of the elongate thermocouple 54 can include a distal end of the elongate thermocouple 54 that has had its wire coating stripped. The stripped portion of the elongate thermocouple 54 (e.g., temperature sensing component) can be adhered within the electrode pocket 45, such that the stripped portion of the elongate thermocouple 54 is located within the electrode pocket 45 and the un-stripped portion of the elongate thermocouple 54 is located in the center cavity within the polymer tube 55.

The distal end of the thermal sensor 36 can be at an angle θ with respect to the longitudinal axis 31 formed by the catheter tip assembly, θ can be in a range of 0 degrees to 30 degrees, in some examples. Allowing for an angle θ to exist between the distal end of the thermal sensor 36 and the horizontal axis 31 can reduce an amount of bend in the distal end of the thermal sensor 36, in turn reducing an amount of stress placed on the thermal sensor at the interface between the center cavity 52 and the electrode cap 29.

Adhesive can be introduced into the electrode pocket 45 such that the adhesive completely and/or partially fills the electrode pocket 45, thus adhering the polymer tube 55 and the distal end of the thermal sensor 36 in the electrode pocket 45. In addition, adhesive can be introduced into the thermocouple lumen 48 to secure the thermal sensor 36 in the thermocouple lumen 48. In an example, the adhesives introduced into the electrode pocket 45 and the thermocouple lumen 48 can have a durometer that allows for flex of the distal end of the thermal sensor 36 within the electrode pocket 45. For instance, the adhesive can have a durometer such as that associated with an M11 adhesive, commercially available from Loctite®. Upon application of the adhesives within the electrode pocket 45 and the thermocouple lumen 48, the adhesive can be cured by heating the adhesive at a temperature in a range of 135 to 150° F., in an example. Alternatively, in some examples, the adhesive can be cured at room temperature.

In some embodiments the proximal stem 38 can comprise an inner surface 57 and a ledge feature 60. The inner surface 57 of the proximal stem 38 can define a manifold lumen through which the manifold assembly 35 can extend. The ledge feature 60 may be an annular or partially annular lip or protrusion from inner surface 57 that is sized and configured to interact with the manifold assembly 35, such that the manifold assembly 35 can be inserted a predetermined distance into the center cavity 52. The ledge feature 60 can comprise a ridge or narrowing of the inner surface 57 of the proximal stem 38. In some embodiments, the ledge feature 60 can comprise a non-continuous feature to restrict the movement of a stop tube 58, which is adhered to the manifold assembly via adhesive 59, past a certain point in the proximal stem 38 of the catheter tip assembly 30. The fluid lumen manifold 35 can include irrigation ports 56, for the passing of irrigation fluid into the center cavity and through irrigation ports 44 and/or linear gap 41, in an example.

In some embodiments, the thermal sensor 36 can be turned or wrapped around a portion of the fluid lumen manifold 35 that extends into the center cavity 52. Such a turned thermal sensor may define a three-dimensional shape that may include a helical or spiral type shape, such as that shown in the figures. In an example, the thermal sensor 36 can be turned or wrapped around a diameter that is between an outer diameter of the fluid lumen manifold 35 and an inner diameter of the electrode wall 40, Which can increase an amount of slack in the thermal sensor 36, thus reducing stress points where the thermal sensor 36 is adhered to the electrode cap 29 and the proximal stem 38.

In some embodiments, the catheter tip assembly 30 can include a coil 53 that extends between the distal end of the proximal stem 38 and the proximal end of the electrode cap 29 and can encircle the thermal sensor 36 and/or the fluid lumen manifold. The coil 53 can be sized and configured such that the coil 53 can be located within the center cavity 52 of the flexible tip electrode 32. The coil can provide structural integrity to the flexible tip electrode and bias the flexible tip electrode 32 into pre-determined arrangements. The coil 53 can bias the flexible tip electrode 32 in a longitudinal direction or in a pre-bent configuration. In one embodiment, the coil 53 can comprise a resilient material such as stainless steel and/or a shape memory material such as nitinol. When flexible tip electrode 32 is at a free length that is unaffected by any force applied to the flexible tip electrode 32, the coil 53 can be partially compressed, in some examples. The partially compressed coil 53 can provide the catheter tip assembly 30 with a return to straight functionality. For example, if a longitudinal and/or lateral force are applied to flexible tip electrode 32, deflecting the electrode wall 40 and/or electrode cap 29 from an initial state, upon removal of the force, the coil 53 will return to its partially compressed state and thus return the electrode wall 40 and/or electrode cap 29 to its initial state.

In some embodiments, changing the path of the thermal sensor 36 in the center cavity from a linear configuration to a configuration where the thermal sensor 36 is turned about the linear axis 31 can result in a change in force that is necessary to compress and/or deflect the flexible tip electrode from an initial orientation. In an example, because more slack is present in the thermal sensor 36 in the turned configuration, the thermal sensor 36 may deform more easily than a thermal sensor in the linear configuration. As such, the coil can have an increased spring force versus a coil used with a thermal sensor 36 in the linear configuration. In some examples, the coil can have a spring force at approximately 0.13 of its compressed length in a range of 15 to 100 grams, although examples are not so limited.

Figure 5A:
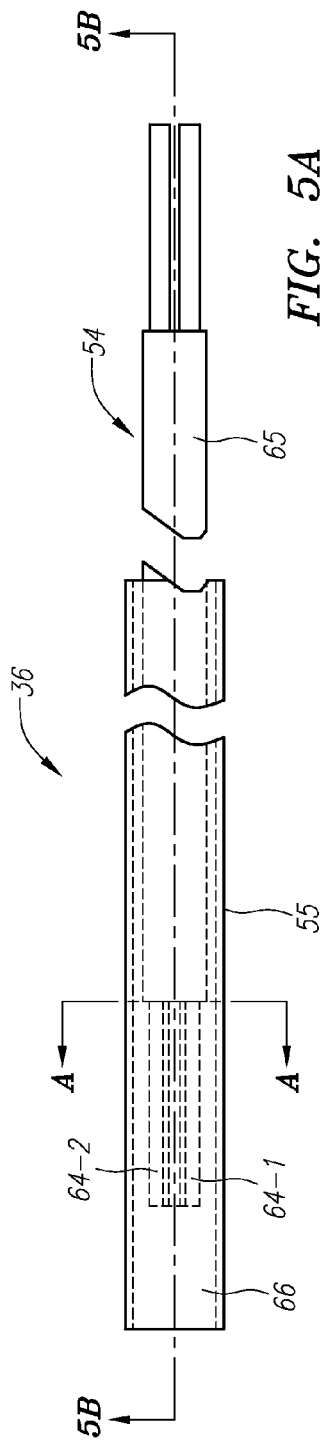
FIG. 5A illustrates a side view of the thermal sensor seen in FIG. 4, in accordance with embodiments of the present disclosure.

FIG. 5A illustrates a side view of the thermal sensor shown in FIG. 4, in accordance with embodiments of the present disclosure. In an example, as discussed herein, the thermal sensor 36 can include an elongate thermocouple 54 adhered within a polymer tube 55. The elongate thermocouple 54 can include thermocouple wires 64-1, 64-2, which can be coated by wire coating 65. As discussed herein, the elongate thermocouple 54 can be adhered within the polymer tube 55 using an adhesive 66. In an example, a solder joint located at the distal end of the elongate thermocouple 54 can be inserted into the electrode pocket 45, as discussed herein, to monitor the operating temperature of the flexible tip electrode 32 and/or the temperature of tissue adjacent the flexible tip electrode 32. In some embodiments, the elongate thermocouple 54 can be stripped of the wire coating 65 distally in relation to line A-A, which can represent an interface between the center cavity 52 and the proximal side of the electrode cap 29 (as shown in FIG. 4). Stripping the wire coating can result in an increased heat transfer between the flexible tip electrode 32 and the solder joint at the distal end of the elongate thermocouple 54 and/or between the tissue adjacent the flexible tip electrode 32 and the solder joint at the distal end of the elongate thermocouple 54, which can provide a more accurate measurement of temperature via the elongate thermocouple 54.

Figure 5B:
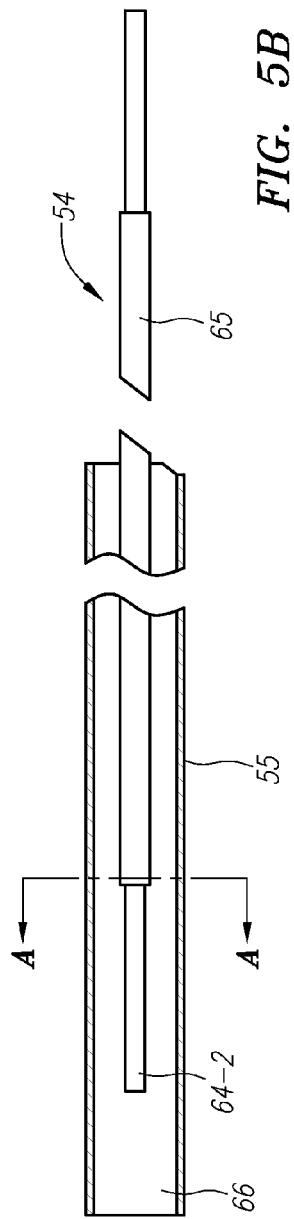
FIG. 5B illustrates a cross-sectional view of the thermal sensor seen in FIG. 5A taken in the direction of line 5B-5B, in accordance with embodiments of the present disclosure.

FIG. 5B illustrates a cross-sectional view of the thermal sensor seen in FIG. 5A taken in the direction of line 5B-5B, in accordance with embodiments of the present disclosure. As discussed herein, the thermal sensor 36 can include the elongate thermocouple 54 adhered within the polymer tube 55 with adhesive 66. From the top view, the thermocouple wire 64-2 can be seen and is coated by wire coating 65. In some embodiments, the elongate thermocouple 54 can be stripped of the wire coating 65 distally in relation to line A-A, which can represent an interface between the center cavity 52 and the proximal side of the electrode cap 29.

Figure 5C:
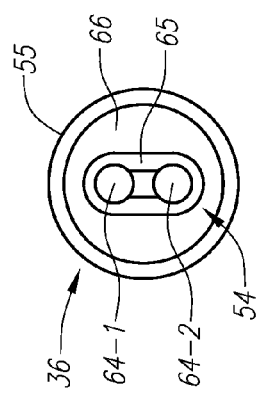
FIG. 5C illustrates an end view of the thermal sensor adhered within the polymer tube seen in FIG. 5A, in accordance with embodiments of the present disclosure.

FIG. 5C illustrates an end view of the thermal sensor adhered within the polymer tube seen in FIG. 5A, in accordance with embodiments of the present disclosure. The thermal sensor 36 can include an elongate thermocouple 54 that includes the thermocouple wires 64-1, 64-2 and the wire coating 65. The elongate thermocouple 54 can be adhered within polymer tube 55 with adhesive 66, which can be, for example, a two-part epoxy. In some examples, spacers can be inserted and/or built into the polymer tube 55 and/or can be placed around the elongate thermocouple 54 prior to inserting the elongate thermocouple 54 into the polymer tube 55. The spacers can center the elongate thermocouple 54 and/or a distal end and/or solder joint at the distal end of the elongate thermocouple 54, which can help in collecting a uniform temperature reading.

Embodiments are described herein of various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment(s) is included in at least one embodiment. Thus, appearances of the phrases "in various embodiments," "in some embodiments," "in one embodiment," or "in an embodiment," or the like, in places throughout the specification, are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Although at least one embodiment for a flex tip fluid lumen assembly with thermal sensor has been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the devices. Joinder references (e.g., affixed, attached, coupled, connected, and the like) are to be construed broadly and can include intermediate members between a connection of elements and relative movement between elements. As such, joinder references do not necessarily infer that two elements are directly connected and in fixed relationship to each other. It is intended that all matter contained in the above description or shown in the accompanying drawings shall be interpreted as illustrative only and not limiting. Changes in detail or structure can be made without departing from the spirit of the disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed:

1. A catheter tip assembly comprising:
   a proximal stem that comprises a lumen;
   an electrode wall that comprises a center cavity, the electrode wall coupled to the distal end of the proximal stem, and wherein the electrode wall is configured to distribute energy to a tissue;
   an electrode cap coupled to a distal end of the electrode wall;
   an elongate thermocouple extending through the lumen of the proximal stem and the center cavity and coupled to the electrode cap, wherein the elongate thermocouple is turned around a portion of a longitudinal axis defined by the catheter tip assembly; and
   a fluid lumen manifold that extends through the lumen of the proximal stem, wherein the elongate thermocouple is turned around the fluid lumen manifold, and wherein a diameter at which the elongate thermocouple is turned around the fluid lumen manifold is between an outer diameter of the fluid lumen manifold and an inner diameter of the electrode wall.

2. The catheter tip assembly of claim 1, wherein:
   a catheter shaft is coupled to a proximal end of the proximal stem; and
   the elongate thermocouple extends from the electrode cap through a lumen of the catheter.

3. The catheter tip assembly of claim 1, wherein the elongate thermocouple is turned around the portion of the longitudinal axis in a range of 0.2 and 1 turn.

4. The catheter tip assembly of claim 1, wherein the elongate thermocouple is turned around the portion of the longitudinal axis between a distal end of the proximal stem and a proximal end of the electrode cap.

5. The catheter tip assembly of claim 1, further comprising a coil that extends between the distal end of the proximal stem and the proximal end of the electrode cap.

6. The catheter tip assembly of claim 5, wherein the coil has a spring force in a range of 15 to 100 grams.

7. The catheter tip assembly of claim 1, wherein the elongate thermocouple is adhered to the electrode cap and the proximal stem.

8. The catheter tip assembly of claim 1, wherein the elongate thermocouple is inserted within a lumen of a formed polymer tube, wherein a distal end of the formed polymer tube is located within an electrode pocket in the electrode cap.

9. A catheter comprising:
   a proximal stem that comprises a manifold lumen and a thermocouple lumen;
   an electrode wall that comprises a center cavity in communication with the manifold lumen and the thermocouple lumen, the electrode wall coupled to a distal end of the proximal stem;
   an electrode cap coupled to a distal end of the electrode wall;
   a fluid lumen manifold that extends through the manifold lumen a defined distance into the center cavity, wherein a distal end of the fluid lumen manifold terminates proximally with respect to the electrode cap; and
   an elongate thermocouple that extends through the thermocouple lumen and is coupled to the electrode cap, wherein the elongate thermocouple is turned around a portion of the fluid lumen manifold, and wherein the elongate thermocouple is turned around a diameter that is between an outer diameter of the fluid lumen manifold and an inner diameter of the electrode wall.

10. The catheter of claim 9, wherein the elongate thermocouple is turned around the portion of the fluid lumen manifold between a distal end of the proximal stem and a proximal end of the electrode cap.

11. The catheter of claim 9, further comprising a catheter shaft coupled to a proximal end of the proximal stem, wherein the elongate thermocouple extends through the catheter shaft to a proximal end of the catheter shaft.

12. The catheter of claim 9, further comprising a coil in the center cavity that extends between the distal end of the proximal stem and the proximal end of the electrode cap, wherein the coil encircles the elongate thermocouple and the fluid lumen manifold.

13. The catheter of claim 9, wherein the manifold lumen and the thermocouple lumen are connected.

14. The catheter of claim 9, wherein the manifold lumen and the thermocouple lumen are separate.

15. A flexible tip electrode comprising:
   a proximal stem that comprises a manifold lumen and a thermocouple lumen;
   a flexible electrode wall that comprises a center cavity and a linear gap, the flexible electrode wall coupled to the distal end of the proximal stem and configured to distribute energy to a tissue;
   an electrode cap coupled to a distal end of the flexible electrode wall;
   a fluid lumen manifold that extends through the manifold lumen a defined distance into the center cavity;
   an elongate thermocouple that extends through the thermocouple lumen and is coupled to the electrode cap, wherein the elongate thermocouple is turned around a portion of the fluid lumen manifold in a range of 0.2 to 1 turn, and wherein the elongate thermocouple is wrapped around a diameter that is between an outer diameter of the fluid lumen manifold and an inner diameter of the electrode wall; and
   a coil in the center cavity that extends between the distal end of the proximal stem and a proximal end of the electrode cap, wherein the coil encircles the fluid lumen manifold and the elongate thermocouple, and wherein a diameter of the coil is between the diameter around which the elongate thermocouple is wrapped and the inner diameter of the electrode wall.

16. The flexible tip electrode of claim 15, wherein:
   the electrode cap comprises an electrode pocket formed in a distal face of the electrode cap that is in communication with the center cavity; and
   a temperature sensing component of the elongate thermocouple is adhered in the electrode pocket formed in the distal face of the electrode cap.

17. The flexible tip electrode of claim 16, wherein the elongate thermocouple is inserted into a polymer tube.

18. The flexible tip electrode of claim 16, wherein the electrode pocket is defined about a longitudinal axis defined by the flexible tip electrode and is located in a center of the electrode cap.

19. The flexible tip electrode of claim 18, wherein:
   the electrode pocket is defined through a distal face of the electrode cap such that the electrode pocket is in communication with a distal side of the electrode cap and the center cavity; and
   a longitudinal axis of the temperature sensing component is disposed at an angle with respect to a longitudinal axis of the flexible tip electrode.

* * * * *